US008996110B2

(12) United States Patent
Sison et al.

(10) Patent No.: US 8,996,110 B2
(45) Date of Patent: Mar. 31, 2015

(54) SYSTEM AND METHOD FOR DETERMINING CAUSE OF IRREGULARITY WITHIN PHYSIOLOGIC DATA

(75) Inventors: Shiloh Sison, Alameda, CA (US); Gabriel A. Mouchawar, Valencia, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 19 days.

(21) Appl. No.: 13/537,714

(22) Filed: Jun. 29, 2012

(65) Prior Publication Data

US 2014/0005496 A1 Jan. 2, 2014

(51) Int. Cl.
| | |
|---|---|
| *A61B 5/11* | (2006.01) |
| *A61B 5/00* | (2006.01) |
| *A61B 5/0402* | (2006.01) |
| *A61N 1/365* | (2006.01) |
| *A61N 1/37* | (2006.01) |
| *A61B 5/042* | (2006.01) |

(52) U.S. Cl.
CPC ............... *A61B 5/721* (2013.01); *A61B 5/1116* (2013.01); *A61B 5/7246* (2013.01); *A61B 5/686* (2013.01); *A61B 5/0006* (2013.01); *A61B 5/0402* (2013.01); *A61N 1/365* (2013.01); *A61N 1/36535* (2013.01); *A61N 1/36542* (2013.01); *A61N 1/3702* (2013.01); *A61B 5/042* (2013.01); *A61B 2560/0223* (2013.01); *A61B 2562/0219* (2013.01)
USPC ......................................................... 607/27

(58) Field of Classification Search
CPC .... A61B 5/721; A61B 5/1116; A61B 5/1118; A61B 5/0205
USPC ................. 607/6, 19, 27; 600/483, 513
See application file for complete search history.

(56) References Cited

U.S. PATENT DOCUMENTS

| | | | |
|---|---|---|---|
| 5,425,750 A | 6/1995 | Moberg | |
| 5,647,379 A * | 7/1997 | Meltzer | 128/897 |
| 5,865,760 A * | 2/1999 | Lidman et al. | 600/509 |
| 6,287,328 B1 * | 9/2001 | Snyder et al. | 600/509 |
| 6,708,063 B2 * | 3/2004 | Czygan et al. | 607/19 |
| 7,996,070 B2 | 8/2011 | Van Dam | |
| 8,180,440 B2 * | 5/2012 | McCombie et al. | 600/513 |
| 2001/0012954 A1 * | 8/2001 | Czygan et al. | 607/11 |
| 2006/0265024 A1 * | 11/2006 | Goetz et al. | 607/48 |
| 2007/0156057 A1 * | 7/2007 | Cho et al. | 600/513 |
| 2008/0091114 A1 * | 4/2008 | Min et al. | 600/508 |
| 2009/0156908 A1 * | 6/2009 | Belalcazar et al. | 600/301 |
| 2009/0259216 A1 * | 10/2009 | Drew et al. | 604/891.1 |
| 2010/0114204 A1 * | 5/2010 | Burnes et al. | 607/4 |
| 2010/0179444 A1 * | 7/2010 | O'Brien et al. | 600/509 |
| 2011/0105927 A1 * | 5/2011 | Greenhut et al. | 600/513 |
| 2011/0148400 A1 * | 6/2011 | Doerr et al. | 324/207.11 |

(Continued)

FOREIGN PATENT DOCUMENTS

WO   WO 2009/036256   3/2009

*Primary Examiner* — Carl H Layno
*Assistant Examiner* — Eugene Wu
(74) *Attorney, Agent, or Firm* — Theresa A. Raymer

(57) ABSTRACT

A method for determining the cause of an irregularity in physiologic data collected by a medical device may include monitoring a collected physiologic characteristic of a patient through the physiologic data, detecting an irregularity in the physiologic data, monitoring position data of the patient, correlating the physiologic data with the position data, and determining the cause of the irregularity in the physiologic data based on correlation of the physiologic data with the position data.

19 Claims, 11 Drawing Sheets

(56) References Cited

U.S. PATENT DOCUMENTS

| | | | |
|---|---|---|---|
| 2012/0004699 A1* | 1/2012 | Bobgan et al. | 607/27 |
| 2012/0083701 A1* | 4/2012 | Osorio | 600/483 |
| 2012/0232416 A1* | 9/2012 | Gilham et al. | 600/515 |

* cited by examiner

SYSTEM AND METHOD FOR DETERMINING CAUSE OF IRREGULARITY WITHIN PHYSIOLOGIC DATA

BACKGROUND OF THE INVENTION

Embodiments generally relate to a system and method for determining causes of irregularities, such as noise, within an implantable medical device (IMD), and more particularly to a system and method for determining causes of irregularities within an IMD through the use of a position detector, such as an accelerometer.

Numerous medical devices exist today, including but not limited to electrocardiographs (ECGs), electroencephalographs (EEGs), squid magnetometers, implantable pacemakers, implantable cardioverter-defibrillators (ICDs), implantable cardiac resynchronization devices (CRTs), implantable cardiac monitors, neurostimulators, electrophysiology (EP) mapping and radio frequency (RF) ablation systems, and the like (hereafter generally "implantable medical devices" or IMDs). IMDs commonly employ one or more leads with electrodes that either receive or deliver voltage, current or other electromagnetic pulses from or to an organ or tissue for diagnostic or therapeutic purposes.

Many IMDs, such as pacemakers and ICDs, are susceptible to noise generated by electromagnetic interference (EMI), myopotential oversensing (for example, signals generated by movement of a patient's arms and chest muscles), and/or intermittent lead fractures. Based on the generated noise, an IMD may deliver an inappropriate therapy, for example.

Typically, a physician reviews the signals from the IMD. For example, a physician may view an intracardiac electrogram (IEGM) or electrocardiogram (ECG) saved within an IMD. The physician may see noise or other such irregularities in the IEGM or ECG, but may not be able to discern the cause of the irregularities. In an effort to determine the nature of the irregularities, the physician may ask the patient about the nature of what he/she was doing at the time of a particular irregularity. However, the patient may not be able to recall what he/she was doing at the time of the irregularity. The physician may then ask the patient to engage in a series of physical movements and maneuvers, such as moving his/her arms, in an effort to recreate the irregularity within the IEGM or ECG. However, the movements and maneuvers may not generate a response signal in the IEGM or ECG that matches the original irregularity. Consequently, the physician may conclude that the noise or irregularity shown in the IEGM or ECG was merely caused by EMI. However, the noise or irregularity may actually have been caused by myopotential oversensing or a lead fracture within the IMD. As such, the physician may miss an opportunity to adapt sensing parameters of the IMD, or recommend a new lead.

SUMMARY

Certain embodiments provide a method for determining the cause of an irregularity in physiologic data collected by a medical device. The method may include monitoring a collected physiologic characteristic of a patient through the physiologic data, detecting an irregularity in the physiologic data, monitoring position data of the patient, correlating the physiologic data with the position data, and determining the cause of the irregularity in the physiologic data based on correlation of the physiologic data with the position data.

The detecting operation may include correlating the irregularity with an aberration in the position data. The irregularity in the physiologic data may include a deviation from a standard baseline, waveform, steady state, template, or pattern.

The correlating operation may include synchronizing the physiologic data with the position data over a common time frame. The correlating operation may include comparing the irregularity in the physiologic data with a flagged event of the position data.

The determining operation may include detecting that the position data that correlates with the irregularity is steady, and determining that electromagnetic interference is the cause of the irregularity based on the steady position data. The determining operation may include detecting that the position data that correlates with the irregularity is associated with known position data readings related to patient movement, and determining that patient movement is the cause of the irregularity based on the known position data readings. The determining operation may include detecting that the position data that correlates with the irregularity is associated with a known patient reading related to one or both of a patient movement or posture, and determining that a lead fracture is the cause of the irregularity based on the known patient reading.

The method may also include continually storing the physiologic data and the position data in a memory of the medical device. For example, the method may include continually storing the physiologic data and the position data in a buffer within a memory of the medical device. Optionally, the method may include storing the physiologic data and the position data in a memory of the medical device upon the detecting operation. The correlating operation may be triggered through the detecting operation.

Certain embodiments provide a medical device including a main housing, a position detector configured to provide position data of the patient, and a controller contained within the main housing. The controller being configured to control operation of the medical device in order to extract physiologic data from a patient. The controller may include inputs to collect position data and physiologic data, a monitoring module configured to receive the position and physiologic data from the inputs and monitor a physiologic characteristic of the patient, an irregularity-detection module configured to detect an irregularity in the physiologic data, a correlation module configured to correlate the physiologic data with the position data, and a cause-determination module configured to determine a cause of the irregularity.

The position detector may be contained with the main housing. As but one example, the position detector may include a 3-axis accelerometer.

The irregularity-detection module may be configured to detect the irregularity by detecting an aberration in the position data. The cause-determination module may be configured to determine that electromagnetic interference is the cause of the irregularity when the position data that correlates with the irregularity is steady. The cause-determination module may be configured to determine that patient movement is the cause of the irregularity when the position data that correlates with the irregularity is associated with known position data readings related to patient movement. The cause-determination module may be configured to determine that a lead fracture is the cause of the irregularity when the position data that correlates with the irregularity is associated with a known patient reading related to one or both of a patient movement or posture.

The medical device may also include a memory within the main housing configured to store the physiologic data and the position data. The controller may be configured to continually store the physiologic data and the position data in the memory. The controller may be configured to continually store the physiologic data and the position data in a buffer within a memory of the medical device. Optionally, the controller may be configured to store the physiologic data and the position data in the memory when the irregularity is detected.

DETAILED DESCRIPTION

Figure 1:
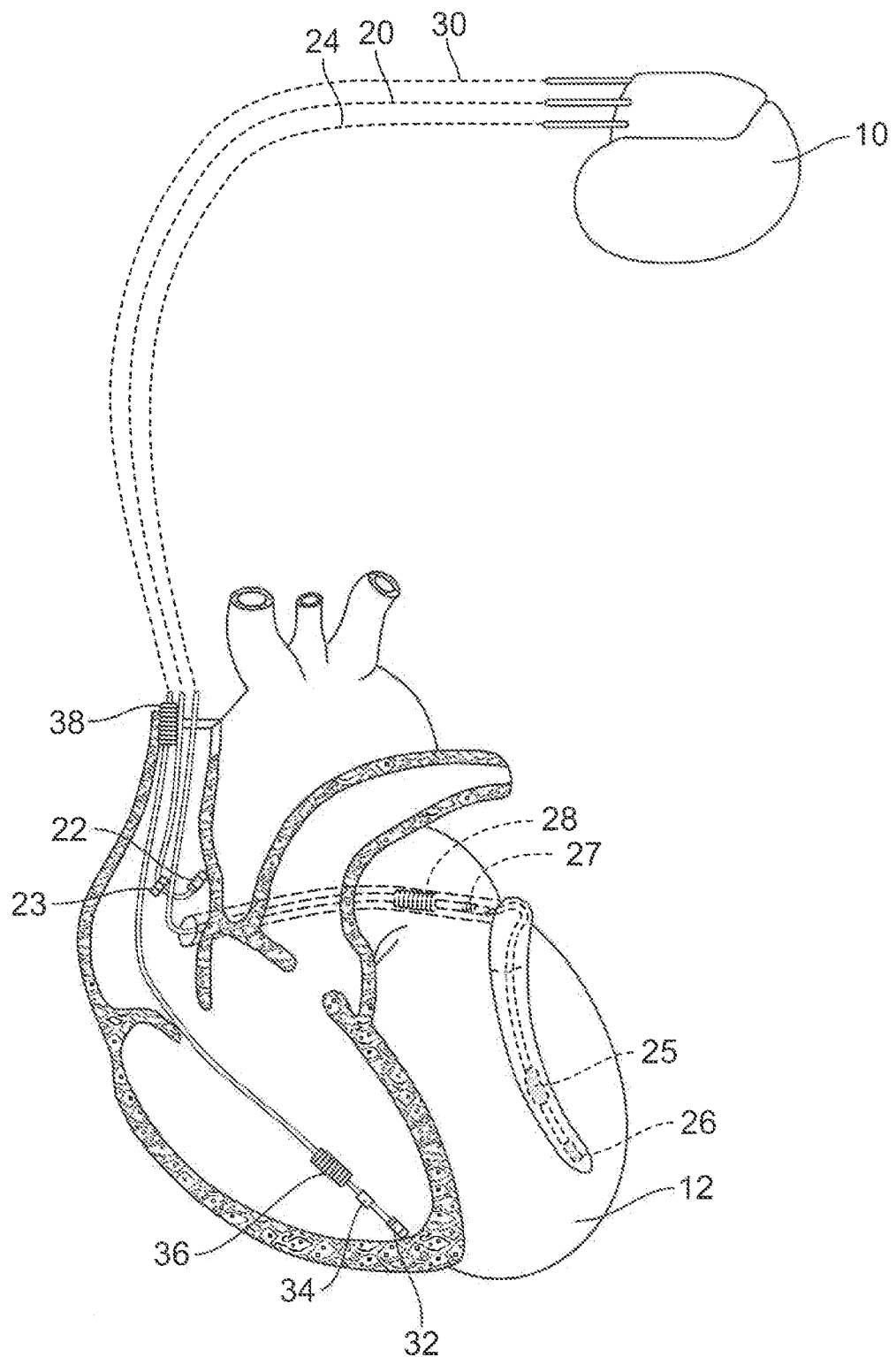
FIG. 1 illustrates a simplified view of an exemplary implantable medical device (IMD) in electrical communication with at least three leads implanted into a patient's heart, according to an embodiment.

FIG. 1 illustrates a simplified view of an exemplary implantable medical device (IMD) 10 in electrical communication with at least three leads 20, 24, and 30 implanted into a patient's heart 12, according to an embodiment. To sense atrial cardiac signals and to provide right atrial chamber stimulation therapy, the IMD 10 may be coupled to an implantable right atrial lead 20 including at least one atrial tip electrode 22 that typically is implanted in the patient's right atrial appendage. The right atrial lead 20 may also include an atrial ring electrode 23 to allow bipolar stimulation or sensing in combination with the atrial tip electrode 22.

To sense the left atrial and left ventricular cardiac signals and to provide left-chamber stimulation therapy, the IMD 10 may be coupled to a lead 24 designed for placement in the "coronary sinus region" via the coronary sinus ostium in order to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the lead 24 is designed to: receive atrial and/or ventricular cardiac signals; deliver left ventricular pacing therapy using at least one left ventricular tip electrode 26 for unipolar configurations or in combination with left ventricular ring electrode 25 for bipolar configurations; deliver left atrial pacing therapy using at least one left atrial ring electrode 27 as well as shocking therapy using at least one left atrial coil electrode 28.

The IMD 10 is also shown in electrical communication with the patient's heart 12 by way of an implantable right ventricular lead 30 including, in the embodiment, a right ventricular (RV) tip electrode 32, a right ventricular ring electrode 34, a right ventricular coil electrode 36, a superior vena cava (SVC) coil electrode 38, and so on. Typically, the right ventricular lead 30 is inserted transvenously into the heart 12 so as to place the right ventricular tip electrode 32 in the right ventricular apex such that the RV coil electrode 36 is positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

The IMD 10 may be one of various types of implantable devices, such as, for example, an implantable pacemaker, implantable cardioverter-defibrillator ("ICD"), defibrillator, cardiac rhythm management ("CRM") device, neurostimulator, electrophysiology ("EP") mapping and radio frequency ("RF") ablation system, or the like.

Figure 2:
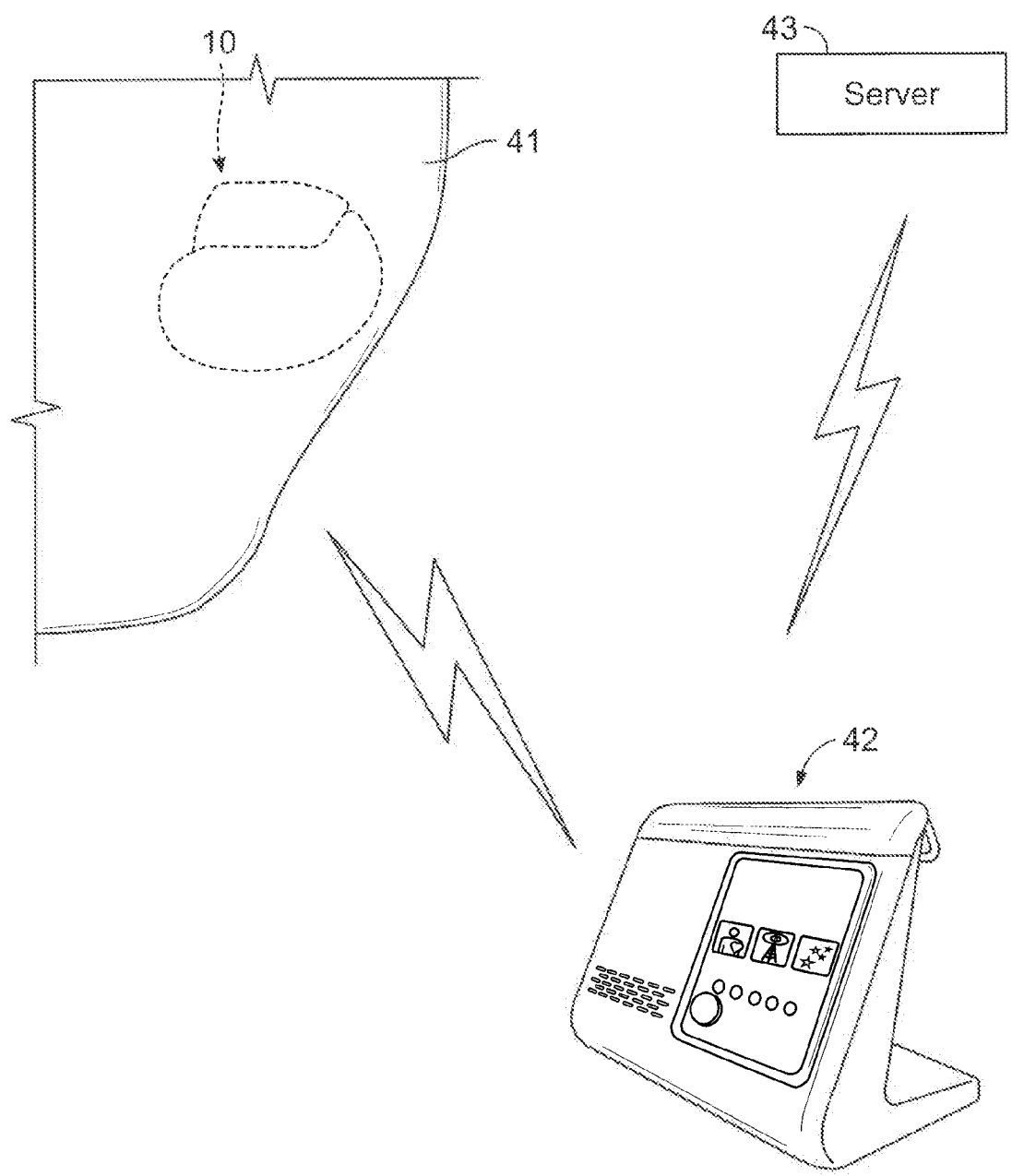
FIG. 2 illustrates a simplified view of an IMD and patient care system (PCS), according to an embodiment.

FIG. 2 illustrates a simplified view of the IMD 10 and a patient care system (PCS) 42, according to an embodiment. The IMD 10 may be located within a patient 41. The remotely-located PCS 42 monitors the IMD 10. The PCS 42 may be located within a home of the patient 41, in his/her vehicle, at his/her office and the like. When, the PCS 42 is located within the patient's home, it may be proximate the patient's 41 bed. The PCS 42 functions as a base station that wirelessly communicates with the IMD 10. The PCS 42 may also communicate with a remote server 43 within a patient care network, such as over a phone link, cellular link, Internet connection, local area network, wide area network and the like.

The PCS 42 performs various functions, such as operating as an intermediate relay device to collect and store patient physiologic data, IMD operational status data and the like. The physiologic data may be electrical data, such as EGM data, for example, related to a physiologic condition, in contrast to position data of a individual. The PCS 42 may then transmit the physiologic data, IMD operational status data and other data to the remote server 43 of the patient care network. Physicians and other personnel can monitor the patient and collect data over the patient care network. Also, the PCS 42 may receive updates, upgrades and other IMD control-related information from the patient care network and relay the IMD control-related information to the IMD 10.

Alternatively, the PCS 42 may not be used. Instead, data from the IMD 10 may simply be accessed at an office of a physician, for example.

Figure 3A:
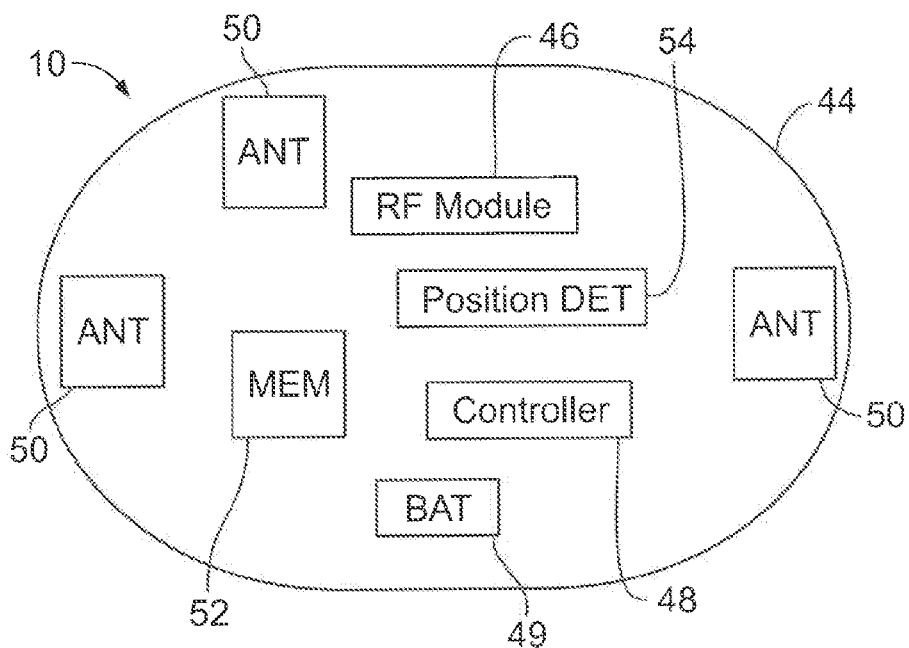
FIG. 3a illustrates a block diagram of an IMD, according to an embodiment.

FIG. 3a illustrates a block diagram of the IMD 10, according to an embodiment. The IMD 10 may include a main housing or body 44 that is configured to be implanted in the patient 41 (shown in FIG. 2). The IMD 10 may contain an RF module 46, such as an RF chip, in electrical communication with a controller 48, memory 52 and one or more antennas 50. The controller 48 is also in communication with a position detector 54, such as an accelerometer. The IMD 10 may be powered through an internal battery 49. The controller 48 may be or include a processing unit, such as a microprocessor, integrated circuit, or the like.

The RF module 46 may be configured to operate in multiple scan modes to search for connection requests from an external device and to establish an RF connection over a predetermined frequency band based on one or more scan attributes. The scan attributes for all available scan modes are loaded into the memory 52.

The RF module 46 may transmit data to and receive data from the PCS 42 through telemetry. The RF module 46 may transmit physiologic data, such as recorded cardiac events, and operational data of the IMD 10 stored in the memory 52 to the PCS 42. Once the data is transmitted from the RF module 46, optionally the data may then be removed from the memory 52 of the IMD 10, as the data is then stored for a longer time frame at the PCS 42 or network server. The data received at the PCS 42 may be used to adjust the settings of the IMD 10. In other words, the PCS 42 may use the received data to adapt the IMD 10 to compensate for changing physiologic circumstances of the patient 41 and/or operations of the IMD 10.

The PCS 42 may also transmit updates, upgrades or other operating data back to the IMD 10. The operating data is then stored in the memory 52, and the controller 48 adjusts operation of the IMD 10 based on the updated operating data.

The position detector 54 may be one of various types of sensors. The position detector 54 may include, for example, an asymmetrical body having one or more electromagnetic, optical, or the like emitters that are configured to be detected by separate receivers. In one example, the position detector 54 may be shaped as an isosceles triangle with sensors or emitters at each vertex. In short, the position detector 54 may include an asymmetrical feature and sensors or emitters positioned on the position detector 54. The asymmetrical feature may allow for easy and ready determination of position. However, any known position detector that may be used to differentiate between vertical and horizontal orientations, for example, may be used.

By way of example, the position detector may be a three-dimensional Micro-Electro-Mechanical-Systems (3D MEMS) sensor. A 3D MEMS sensor may be fabricated in a tiny piece of silicon, capable of measuring acceleration in three orthogonal directions. Using the 3D MEMS sensor, the IMD 10 affords accurate inclination angle (e.g., within 1 arc minute) measurement, with mechanical damping for use in environments subject to strong vibration. The power requirements of the 3D MEMS sensors are extremely low, which gives them a significant advantage in battery-operated IMDs 10 (e.g., microampere average power consumption).

The position detector 54 may be used to sense the posture state of the patient 41 and produce position data. The position detector 54 may produce, as the position data, raw analog or digital signals representative of X-axis, Y-axis and Z-axis orientation and/or translation of the patient relative to a coordinate system or reference item (e.g., direction of gravitational force, true magnetic North, etc.). Optionally, the position detector 54 may produce, as the position data, a resultant orientation and/or translation measurement, such as pitch, yaw and roll angular orientations and/or X, Y, and Z translation relative to reference coordinates or a reference item (e.g., direction of gravitational force). For example, based on calibrated X-, Y-, and Z-axes, sensed by the position detector 54, the controller 48 is able to determine the actual posture, such as vertical or horizontal, and relative movement of the patient 41. The controller 48 may manually or automatically calibrate the IMD 10 to monitor for potential posture states including one or more of a supine state, prone state, right side position, or left side position, as well as changed in posture state or position and/or abrupt changes in posture state or position.

The position data may include information regarding the posture state, relative movement, and rate of change of position of the patient. For example, the position data may indicate that the patient is upright and moving his/her arms at a particular rate. Additionally, for example, the position data may indicate that the patient is upright and stretching his/her arms overhead for a period of time.

The position detector 54 may also be configured to detect various other movements. For example, the position detector 54 may be able to detect when an individual is exercising, whether low-impact or high-impact. Additionally, the position detector 54 may detect abrupt and jarring motions, such as when an individual is traveling in an automobile on a bumpy road, for example.

Figure 3B:
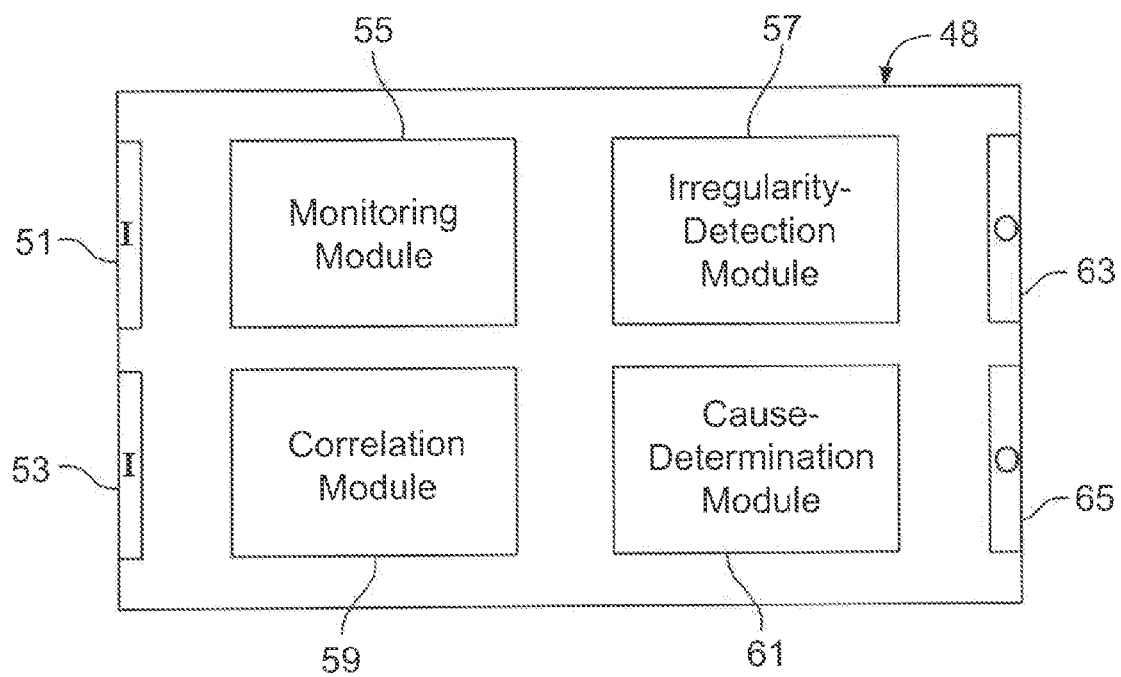
FIG. 3b illustrates a block diagram of a controller, according to an embodiment.

FIG. 3b illustrates a block diagram of the controller 48, according to an embodiment. The controller 48 may include inputs 51 and 53 to collect position data and physiologic data. For example, the input 51 may receive physiologic data and the input 53 may receive position data. The controller 48 may also include a monitoring module 55 configured to receive the position and physiologic data from the inputs 51 or 53 and monitor a physiologic characteristic of a patient. Next, the controller 48 may also include an irregularity-detection module 57 configured to detect an irregularity in the physiologic data, and a correlation module 59 configured to correlate the physiologic data with the position data. The controller 48 may also include a cause-determination module 61 configured to determine a cause of the irregularity. Outputs 63 and 65 may be configured to output data, such as the physiologic data, position data, correlated data, cause data, and the like to one or more of the antennas 50 in order to transmit the output data to an external device, for example.

The irregularity-detection module 57 may be programmed to detect an irregularity by detecting an aberration in the position data. The aberration may be a deviation from a known baseline, template, waveform, or the like. For example, the aberration may be a deviation from a regular, repeating baseline, or a straight baseline.

The cause-determination module 61 may be programmed to determine that electromagnetic interference is the cause of an irregularity when the position data that correlates with the irregularity is steady (or otherwise does not deviate from a known baseline, template, waveform, or the like). The cause-determination module 61 may be programmed to determine that patient movement is the cause of an irregularity when the position data that correlates with the irregularity is associated with known position data readings related to patient movement. Additionally, the cause-determination module 61 may be programmed to determine that a lead fracture is the cause of the irregularity when the position data that correlates with the irregularity is associated with a known patient reading related to one or both of a patient movement or posture.

Figure 4:
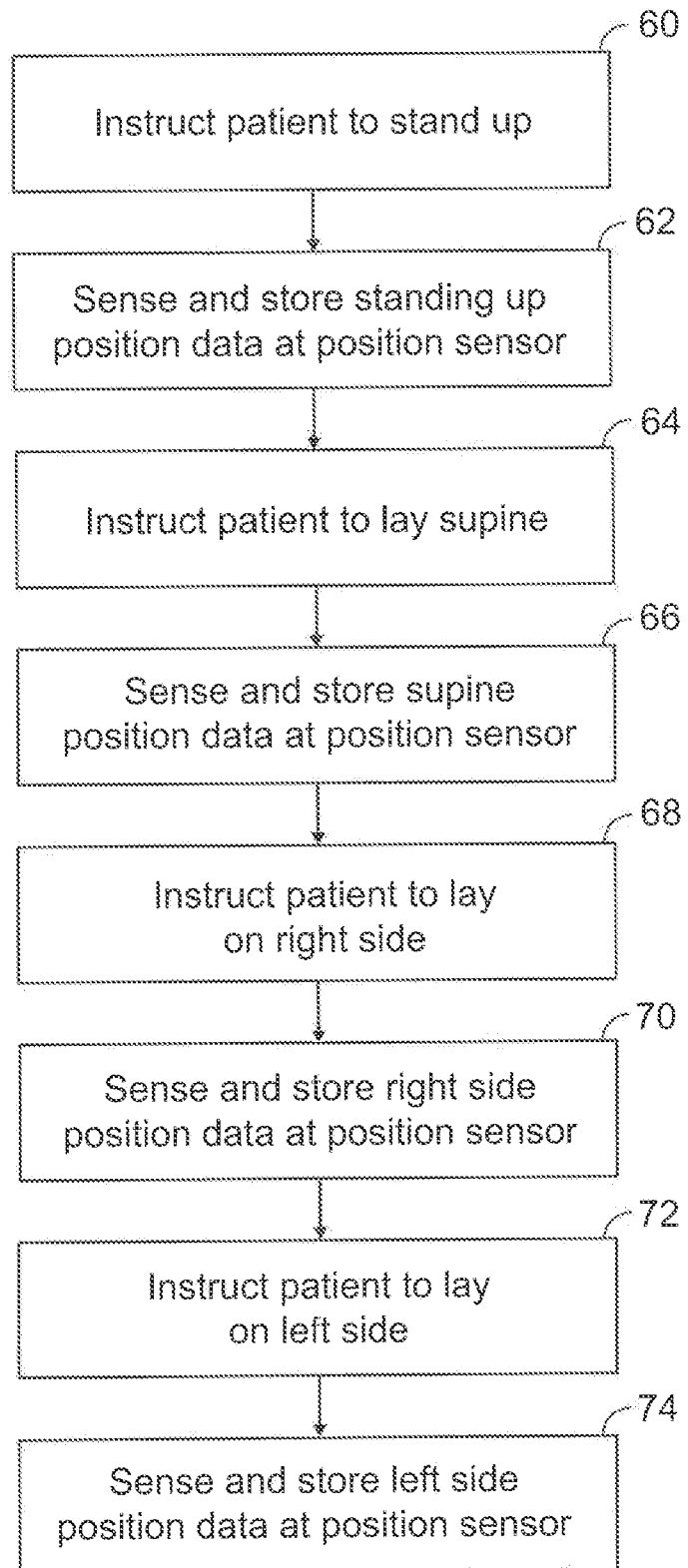
FIG. 4 illustrates a flow chart of a process for calibrating a position detector, according to an embodiment.

FIG. 4 illustrates a flow chart for a process of calibrating the position detector 54, according to an embodiment. At 60, the patient 41 having the implanted IMD 10, stands up and, at the command of the operator, the external programmer or PCS 42 transmits a vertical state condition to the IMD 10 to inform the IMD 10 that the present readings by the position detector 54 correspond to the potential posture state of standing up or vertical. Next at 62, posture signals from the position detector 54 are sensed for a test interval (e.g., 30 sec., 1 minute, 20 minutes). The posture signals for the current test interval are recorded as a calibrated potential posture state. For example, the potential posture state may constitute a single value or set of values representing integration of the posture signal over the test interval. Optionally, the potential posture state may represent a single posture signal or an average of multiple posture signals for the test intervals. At 62, the X, Y, and Z positions and/or orientations of the position detector 54, while the patient 41 is standing, are also stored as vertical state reference coordinates.

At 64, the patient 41 is instructed to lay supine and the external programmer or PCS 42 transmits a horizontal state condition to the IMD 10 to inform the IMD 10 that the present readings by the position detector 54 correspond to the potential posture state of laying down or horizontal. At 66, the X, Y, and Z positions and/or orientations of the position detector 54, while the patient 41 is lying supine, are sensed and stored as horizontal reference coordinates.

At 68, the patient 41 is instructed to lay on his/her right side and the external programmer or PCS 42 transmits a right side state condition to the IMD 10 to inform the IMD 10 that the present readings by the position detector 54 correspond to the potential posture state of laying on the right side. At 70, the X, Y, and Z positions and/or orientations of the position detector 54, while the patient 41 is lying on his/her right side, are sensed and stored as right side reference coordinates. At 72, the patient 41 is instructed to lay on his/her left side and the external programmer transmits a left side state condition to the IMD 10 to inform the IMD 10 that the present readings by the position detector 54 correspond to potential posture states of laying on the left side. At 74, the X, Y, and Z positions and/or orientations of the position detector 54, while the patient is lying on his/her left side, are sensed and stored as left side reference coordinates. In this manner, the position detector 54 is calibrated with respect to upright, supine, and side-lying down positions relative to a reference coordinate system such as defined by gravity. For example, the horizontal axis may be perpendicular to the direction of gravity, while the vertical axis is parallel to the direction of gravity.

Various other postures, movements, and orientations of the patient may also be calibrated. For example, the posture, movement, and/or orientation of the patient reaching his/her hands over his/her head, extending an arm across his/her chest, bending over, and the like, may also be calibrated. The calibration may also be performed using a subset of the measurements discussed above. For example, the calibration may be performed through supine and left side recordings.

Referring again to FIG. 3, as the name suggests, the position detector 54 may detect a posture of a patient 41, in which the IMD 10 is implanted. As noted above, the position detector 54, once calibrated, is used to discern potential posture states and to identify an actual posture state between upright, supine, and right side, left side positions/orientations, bent over, as well as movements such as stretching with arms overheard, extending arms across the chest, and the like.

Figure 5:
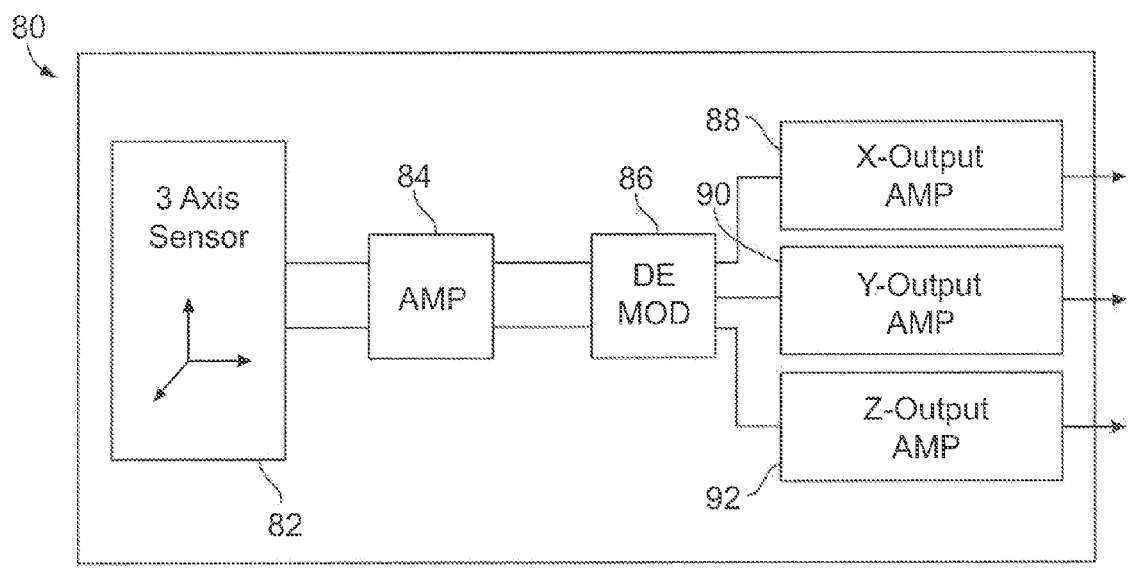
FIG. 5 illustrates a functional block diagram of a position detector, according to an embodiment.

FIG. 5 illustrates a functional block diagram of a position detector 80, according to an embodiment. The position detector 54 shown in FIG. 3 may be, or include, the position detector 80. The position detector 80 may be a 3-axis accelerometer that includes a 3-axis sensor 82 operatively connected to a signal amplifier 84, which may, in turn, be connected to a demodulator 86. The demodulator 86 is, in turn, connected to an X-output amplifier 88, a Y-output amplifier 90, and a Z-output amplifier 92.

In operation, the 3-axis sensor 82 detects the position and motion of a patient. A position signal from the 3-axis sensor 82 is then sent to the amplifier 84, which amplifies the position signal before passing the position signal to the demodulator 86. The demodulator 86 then demodulates the position signal based on X-, Y-, and Z-components, and sends the respective signals to the X-, Y-, and Z-output amplifiers 88, 90, and 92. The signals from the output amplifiers 88, 90, and 92 are then sent to a controller, such as the controller 48 within the IMD 10.

Alternatively, the position detector 80 may include more or less components than those shown. For example, the position detector 80 may include an analog-to-digital converter, digital or analog filters, memory, logic for calculating posture, movements, and orientations, and the like. Additionally, alternatively, the position detector 80 may not include the amplifier or the demodulator. For example, the 3-axis sensor 82 may be directly connected to an output amplifier.

Figure 6:
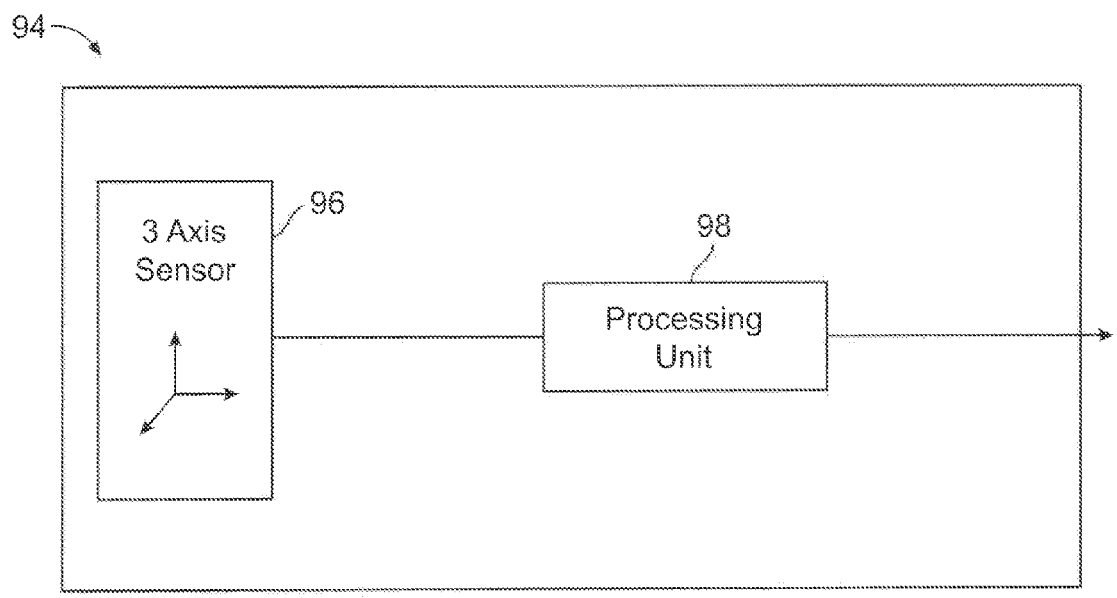
FIG. 6 illustrates a functional block diagram of a position detector, according to an embodiment.

FIG. 6 illustrates a functional block diagram of a position detector 94, according to an embodiment. The position detector 54 shown in FIG. 3 may be, or include the position detector 94.

The position detector 94 may be a 3-axis accelerometer having a 3-axis sensor 96 directly connected to an internal processing unit 98, which may be or include a microprocessor, microcontroller, integrated circuit, and the like. Position signals sensed by the 3-axis sensor 96 may be sent to the processing unit 98, which may then pass the position signals to the controller 48 of the IMD 10.

Alternatively, instead of having a separate, internal processing unit 98, the position detector 94 may include the 3-axis sensor 96 that is in direct communication with the controller 48 of the IMD 10.

Referring to FIGS. 5 and 6, the position detectors 80 and 94 may be various types of accelerometers. For example, instead of a 3-axis accelerometer, the position detector may be a single or dual axis accelerometer. However, a 3-axis accelerometer provides position data with respect to X-, Y-, and Z-axes, as opposed to merely a single axis.

The position detector 54 may be or include a Kynar accelerometer, a quartz or ceramic accelerometer, a piezoelectric accelerometer, or the like. The position detector 54 may be contained within a housing of the IMD 10. Optionally, the position detector 54 may be an integral part of the housing of the IMD 10, for example.

Referring again to FIG. 3, in operation, when an irregularity such as noise (for example, electrical and/or magnetic interference that causes an irregularity in an electrogram or ECG reading), or an abrupt change in position or motion, occurs, the IMD 10 stores the corresponding physiologic data, such as an IEGM or ECG, indicating the irregularity in the memory 52. The irregularity may be a deviation from a standard baseline, waveform, steady state, pattern, or the like. Simultaneously, the IMD 10 stores position data from the position detector 54 in the memory 52 and correlates the position data with the irregularity in the physiologic data. For example, the position data may be correlated with a particular time of an IEGM or ECG when the irregularity appears. Alternatively, position data from the position detector 54 and physiologic data of the IMD 10 may continually be stored and correlated with one another. In one embodiment, when the position detector 54 is an accelerometer, the position data may be one-dimensional data. For example, the position detector 54 may generate position data related to patient movement with respect to a single axis, such as an X-axis, Y-axis, or Z-axis, and transmit the data at a relatively high data rate, for example, 500 Hz. Alternatively, the position data may be two-dimensional data. For example, the position detector 54 may generate position data with respect to two axes. Optionally, the position data may be three-dimensional data (through use of a 3-axis accelerometer). In general, position data with respect to all three axes provides more detail than position data with respect to only one or two axes. However, because the position data with respect to all three axes includes more information, the position data may be transmitted at a slower rate.

For example, if the IMD 10 is configured to generate an IEGM or ECG for a patient, the IEGM or ECG data is stored in the memory 52 over a particular time frame. At the same time, position data from the position detector 54 is also tracked and stored over the same time frame. Consequently, if any irregularities appear on the IEGM or ECG, the position data that is correlated with the IEGM or ECG may provide information to a physician as to the source of the irregularity. For example, the position data may relate to a patient in a supine position. The position data may relate to a patient moving his/her arms. The physician may be able to determine the cause of the irregularity by instructing the patient to engage in a series of maneuvers and movements. The maneuvers and movements, as instructed by the physician, are then detected by the position detector 54, which may then produce a similar reading as the position data that is correlated with the irregularity on the ECG. In this manner, the physician is able to precisely determine the cause of an irregularity within a physiologic data of the IMD 10 through the position data that is correlated with the physiologic data. Therefore, the position data from the position detector 54 provides a snapshot of what happened (for example, the physical environment or occurrence experienced by the patient) at the time of the noise or irregularity episode within the physiologic data, such as an IEGM or ECG.

As explained above, the IMD 10 provides physiologic data, such as an IEGM or ECG, separately and distinctly from the position data output from the position detector 54. The position data may not be directly integrated into the physiologic data, such as an IEGM or ECG. Instead, the position data is correlated over the same time frame as the physiologic data. For example, the physiologic data, such as an IEGM or ECG, may be displayed above a separate and distinct position data display. The physiologic and position displays may be synchronized over a common time frame axis.

The physiologic data may include intracardiac electrogram (IEGM) or electrocardiograph (ECG) data. Alternatively, the physiologic data may be pacing data from a pacemaker, Holter monitor data, defibrillation data from an ICD, and/or various other physiologic data. Additionally, instead of an IMD 10, the device may be an external medical device, such as a Holter monitor.

Thus, in contrast to previous methods and systems, a physician may view an IEGM or ECG, for example, of a patient, and view position data that is directly correlated with the ECG over the same time frame. Whether or not the patient recalls what he/she was doing at the time of an irregularity in the ECG, the correlated position data provides the physician reliable information as to the activity of the patient. The position data allows the physician to determine what the patient was doing at the time of the irregularity. For example, the physician may instruct the patient to move his/her arms in circular movements. If the reading from the position detector 54 during such movement matches the position data that is correlated with the irregularity in the ECG, the physician may then determine that the irregularity was caused by myopotential oversensing, for example. Therefore, the physician may adapt the IMD 10 to disregard such an irregularity. Also, the position data may be directly linked to a lead fracture, which the physician may then remedy.

Additionally, if the irregularity in the physiologic data, such as an IEGM or ECG, is not correlated with any change in position data, then the physician may determine that the irregularity was caused by EMI.

Figure 7A:
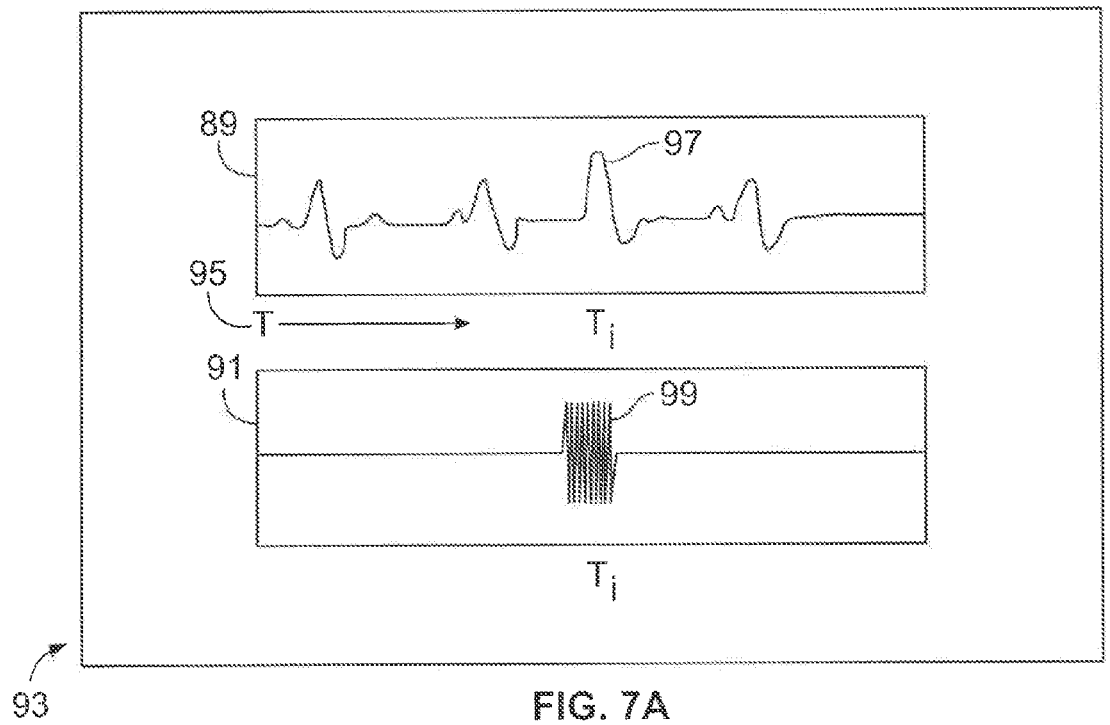
FIG. 7a illustrates a simplified view of a physiologic data correlated with position data on a display, according to an embodiment.

FIG. 7a illustrates a simplified view of physiologic data 89 correlated with position data 91 on a display 93, according to an embodiment. The physiologic data 89 is shown as an ECG. However, this is for illustrative purposes only. The physiologic data 89 may be various other types of data generated by various other types of medical devices.

As shown, the physiologic data 89 is above the position data 91 on the common display 93. Optionally, the physiologic data 89 may be below or the side of the position data 91. A time axis 95 between the physiologic data and the position data 91 is common to both data 91. However, the physiologic data 89 and the position data 91 need not be on a common display. Instead, the physiologic data 89 and the position data 91 may be on separate and distinct displays, or may be on separate and distinct print-outs. In such an embodiment, the separate and distinct physiologic data 89 and the position data 91 may have separate and distinct, but synchronized time axes.

As shown in FIG. 7a, at time $T_i$, an irregularity 97 appears in the physiologic data 89. At the same time $T_i$, an aberration or change 99 appears in the position data 91. The aberration 99 is synched with the irregularity 97. Therefore, the aberration 99 provides information as to the nature of the irregularity 97. The aberration 99 may share similar characteristics to a data readout from the position detector 54 when the patient moves his/her arms, for example. The aberration 99 may share similar characteristics to a data readout from the position detector 54 when the patient stretches his/her arms over his/her head. The aberration or change 99 may be a deviation from a standard or known waveform, baseline, template, steady state signal, or the like. For example, a patient at rest may produce position data having a constant and regular straight or repeating baseline. The aberration or change 99 may be deviations from the straight or repeating baseline.

Figure 7B:
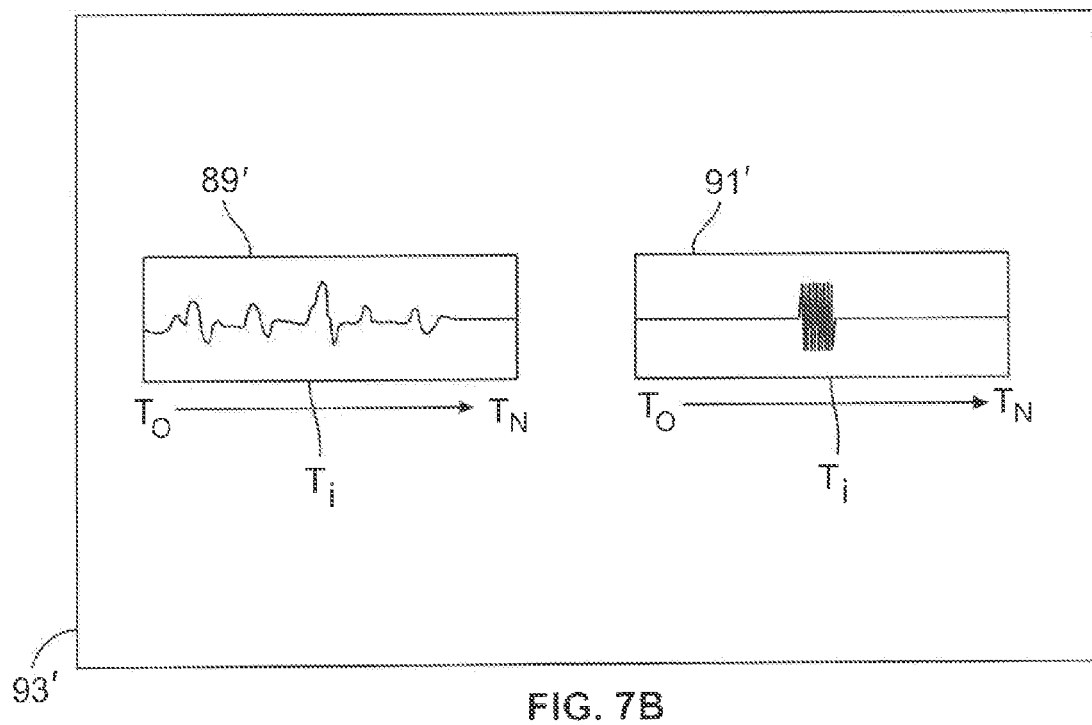
FIG. 7b illustrates a simplified view of a physiologic data correlated with position data on a display, according to an embodiment.

FIG. 7b illustrates a simplified view of physiologic data 89' correlated with position data 91' on a display 93', according to an embodiment. The physiologic data 89' is shown as an ECG. In this embodiment, the physiological data 89' and the position data 91' are shown side-by-side with respect to each other. In general, the position data and physiologic data may be displayed in various other configurations and orientations. In each configuration, the physiologic data and the position data may be synchronized.

Figure 8:
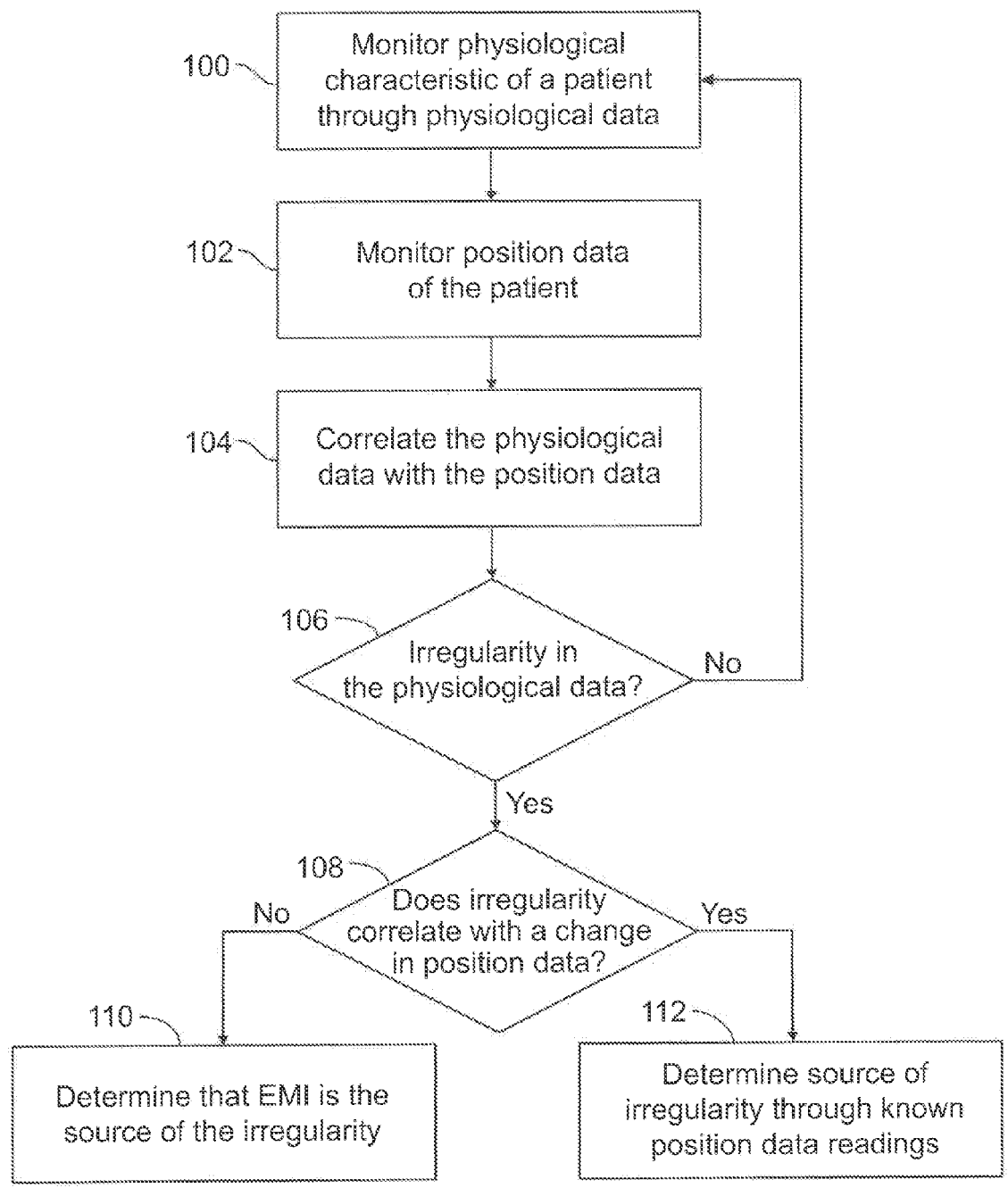
FIG. 8 illustrates a flow chart of a method of determining the source of an irregularity in physiologic data, according to an embodiment.

FIG. 8 illustrates a flow chart of a method of determining the source of an irregularity in physiologic data, according to an embodiment. At 100, a physiologic characteristic (such as heart rate) of a patient is monitored through physiologic data, such as an ECG or an IEGM. For example, an ECG may monitor cardiac signals of a patient. Optionally, an implantable pacemaker may provide a pacing signal to the heart of a patient. The physiologic data is generated by an IMD, such as described above, and/or an external medical device, such as a Holter monitor.

At 102, position data of the patient is also tracked and monitored. The position data may be monitored through a position detector, as described above. The position data and the physiologic data may be simultaneously tracked and recorded in the memory of a medical device, such as an IMD.

At 104, the physiologic data is correlated with the position data over the same time frame. For example, the physiologic data and the position data may be synchronized with respect to one another. Thus, the physiologic data and the position data may both begin at a particular time, and end at a particular time. Therefore, events that occur over the time frame are synchronized with respect to one another. For example, a heart rate or waveform at a particular time $T_1$ is correlated with position data at the same time $T_1$.

Next, at 106, the physiologic data is reviewed to determine if an irregularity, such as noise, exists. The physiologic data may be reviewed by a physician for the irregularity, or the physiologic data may be automatically reviewed by the controller of an IMD, for example, which may be programmed to determine irregularities in the physiologic data. If no irregularity exists, the process returns to 100.

For example, the physiologic data may be reviewed to detect a deviation from a known, accepted, or standard steady state, baseline, template, or the like. For example, an IEGM may have a characteristic steady waveform. The controller of an IMD may be programmed to recognize the steady state. Any deviation from the steady state may trigger an indication of an irregularity. The controller may compare the physiologic data to a standard template, allowable range of rates, waveform slew rates, and/or frequency content, for example. Deviation from the template may trigger the indication of the irregularity.

If, however, an irregularity is present, the process continues to 108, in which it is determined whether the irregularity correlates with a change or aberration in position data. For example, a physician may review the physiologic and position data. If the physician sees an irregularity in the physiologic data (such as a deviation from an accepted heart rate waveform), the physician may review the position data to see if an aberration, such as a deviation from an accepted baseline, exists. Optionally, the controller of the IMD may monitor both the physiologic and position data for irregularities, such as deviations from accepted or known waveform and/or baseline. Again, 108 may be determined by the physician, or automatically through the controller of the IMD, which may be programmed to detect whether an aberration or change in position data corresponds to an irregularity within the physiologic data.

For example, the position data may be reviewed to detect a deviation from a known, accepted, or standard steady state, baseline, template, or the like. For example, the position data of a patient at rest may have a characteristic steady baseline. The controller of an IMD may be programmed to recognize the baseline. Any deviation from the baseline may trigger an indication of an irregularity. The controller may compare the position data to a standard template. Deviation from the template may trigger the indication of the irregularity.

If the irregularity does not correlate with a change or aberration in the position data (that is, the position data remains steady, unchanged, and/or constant with respect to a known or accepted baseline, for example), then at 110, the physician and/or the controller of the IMD may determine that EMI is the source of the irregularity. For example, if EMI is the source of the irregularity, the EMI may produce little to no motion in the position detector 54.

If, however, the irregularity does correlate with a change or aberration in position data, then at 112, the physician and/or IMD may determine the source of the irregularity through known position data readings. For example, the memory of the IMD may store a series of position data readings for various physical movements. Myopotential oversensing, for example, may be characterized by detected position data due to muscle motion within the chest and/or diaphragm of a patient. For example, myopotential oversensing may be characterized by a patient moving his/her arms up, down, side-to-side, or the like, and/or laborious breathing, grunting, coughing, or other such movements that tighten the diaphragm, which causes muscles in the chest to move.

Additionally, the memory of the IMD may store position data readings that occur when a lead fracture is present. For example, the lead fracture may be characterized by motion detected through the position detector 54, as well as a specific posture of the patient. If a patient stretches his/her arms over his/her head, the lead of an IMD may stretch and expose a fracture. When an irregularity, such as noise, is shown within physiologic data, the correlated position data may relate to a patient stretching, for example. Such position data correlated with the irregularity may indicate the presence of a lead fracture.

The physiologic data and the position data may be continually tracked and recorded over a particular time frame, such as the life of an IMD. Stored information, such as stored physiologic data and stored position data, may be sent to an external device through telemetry, as discussed above. After the information is sent to the external device, the information may be erased from the memory of the IMD.

Optionally, the irregularity itself may trigger recordation and correlation of physiologic data and position data. For example, a medical device, such as an IMD, may be programmed to detect an irregularity, such as when physiologic data deviates from a known and standard waveform, for example. When the IMD detects the irregularity, the IMD stores the physiologic data and the position data at that time. The memory of the IMD may include a short term, rolling memory, such as a buffer, in order to continually store a short term memory frame, such as over a 2 minute time frame, within short term memory. When an irregularity is detected, the position data and the physiologic data at the time of the irregularity are then stored in long term memory, and/or sent to external device through telemetry.

In another embodiment, the IMD may store features, parameters, or characteristics of physiologic and position data, as opposed to storing such data over a long time period. For example, if physiologic data exceeds a steady state or baseline for a predetermined period of time, such as 2 minutes, the IMD may store data, including a time stamp, time of day, and duration of event that exceeds the baseline or threshold within memory. The IMD may also store data that includes a description of a patient's posture, such as a forward-backward tilt angle, left-right tilt angle, or the like. In this manner, instead of storing and transmitting position data over a time frame, the IMD may simply store the date, time, and duration of an irregularity as a flagged event, which may then be correlated with the physiologic data. For example, if the physiologic data shows an irregularity at a particular time, a flagged event from the position data may be referenced in order to determine the cause of the irregularity. If there is no flagged event, then it may be determined that EMI is the source of the irregularity. However, if there is a flagged event at a time that corresponds to the irregularity in the physiologic data, then the source of the irregularity may be determined to be something other than EMI.

Figure 9:
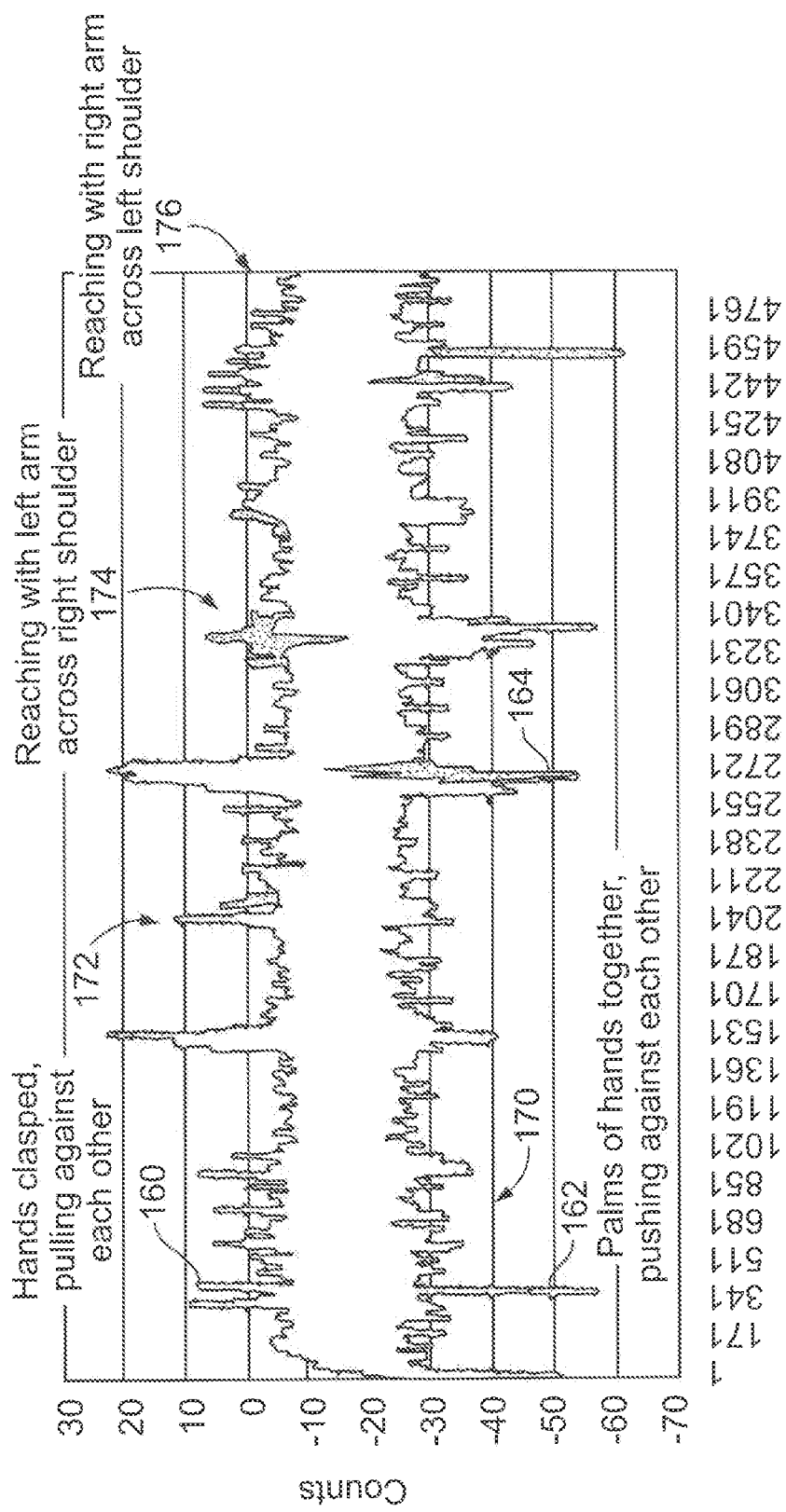
FIG. 9 illustrates a graph of position data output from a position detector during myopotential isometric movements, according to an embodiment.

FIG. 9 illustrates a graph of position data output from a position detector during myopotential isometric movements, according to an embodiment. The horizontal axis relates to samples over time, while the vertical axis relates to counts, or the number of digital bits of equivalent voltage generated by the position detector. FIG. 9 illustrates the output of a 3-axis accelerometer with respect to three dimensions, namely an X-axis 160, Y-axis 162, and Z-axis 164. As shown, when a patient clasps his/her hands and pulls both hands with respect to one another, the position detector generates a characteristic response 170 with respect to the axes 160, 162, and 164. When the patient pushes his/her palms together, the position detector generates a characteristic response 172 with respect to the axes 160, 162, and 164. When the patient reaches with his/her left arm across his/her right shoulder, the position detector generates a characteristic response 174 with respect to the axes 160, 162, and 164. When the patient reaches with a right arm across a left shoulder, the position detector generates a characteristic response 176 with respect to the axes 160, 162, and 164. Various other physical movements may be performed and measured by the position detector. The various characteristics may be stored in the medical device so that when the position detector outputs similar characteristic response, the controller may readily discern the nature of the movements.

Figure 10:
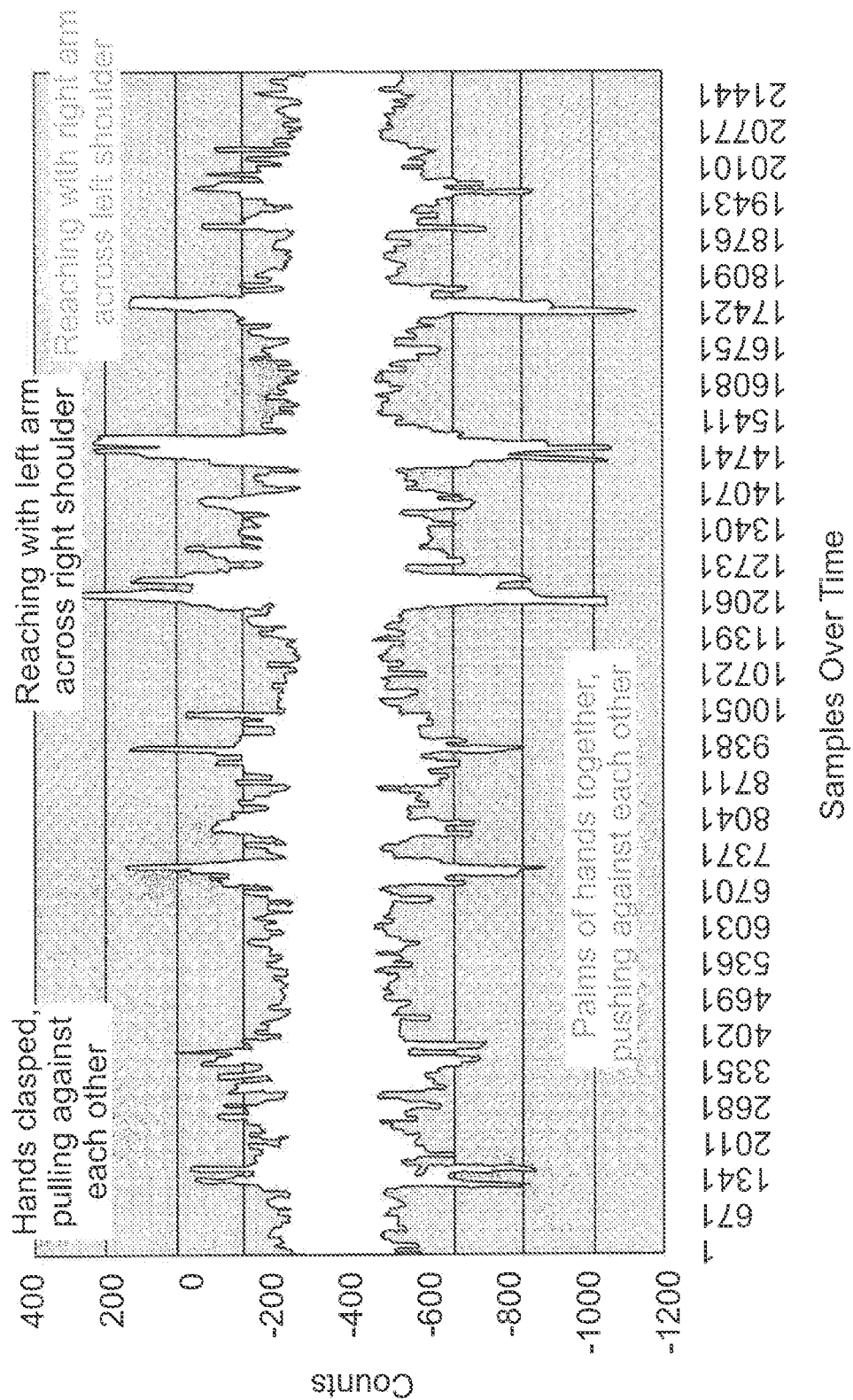
FIG. 10 illustrates a graph of position data output from a position detector during myopotential isometric movements, according to an embodiment.

FIG. 10 illustrates a graph of position data output from a position detector during myopotential isometric movements, according to an embodiment. The graph is similar to that of FIG. 9, except, instead of outputting three-dimensional data, the position detector may alternatively output 1-dimensional data at a higher rate and higher sensitivity.

Referring to FIGS. 9 and 10, the position data may be synchronized and displayed along with physiologic data, such as IEGM or ECG data. The position detector may also be used to calculate the posture of a patient over time during an irregularity of the physiologic data. The posture information may also be synchronized and displayed along with the position data and the physiologic data. Posture information may be used to detect lead failures if it is found that similar postures frequently generate an irregularity in the physiologic data.

As noted above, the medical device, such as the IMD 10, may be used in conjunction with a telemetry system.

Figure 11:
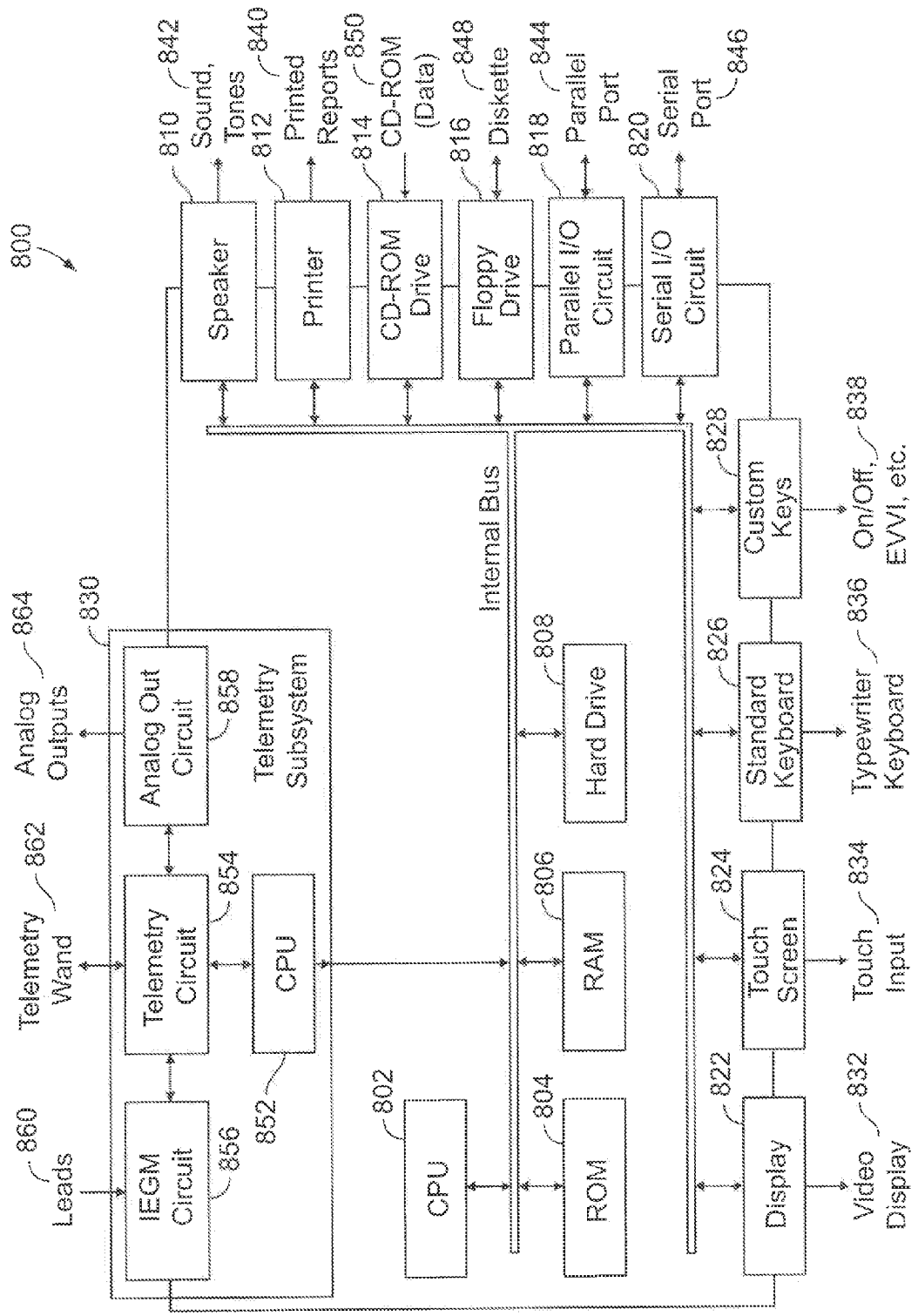
FIG. 11 illustrates a functional block diagram of an external device that is operated in accordance with the processes described herein and to interface with implantable medical devices as described herein.

FIG. 11 illustrates a functional block diagram of an external device 800 (e.g., a PCS or programmer) that is operated in accordance with the processes described herein and to interface with implantable medical devices as described herein. The external device 800 (PCS or programmer) may be a workstation, a portable computer, an IMD programmer, a PDA, a cell phone and the like. The external device 800 includes an internal bus that connects/interfaces with a Central Processing Unit (CPU) 802, ROM 804, RAM 806, a hard drive 808, a speaker 810, a printer 812, a CD-ROM drive 814, a floppy drive 816, a parallel I/O circuit 818, a serial I/O circuit 820, a display 822, a touch screen 824, a standard keyboard connection 826, custom keys 828, and a telemetry subsystem 830. The internal bus is an address/data bus that transfers information between the various components described herein. The hard drive 808 may store operational programs as well as data, such as waveform templates and detection thresholds.

The CPU 802 typically includes a microprocessor, a microcontroller, or equivalent control circuitry, designed specifically to control interfacing with the external device 800 and with the medical device, such as the IMD 10 (shown in FIGS. 1-3). The CPU 802 may include RAM or ROM memory, logic and timing circuitry, state machine circuitry, and I/O circuitry to interface with the IMD 10. The display 822 may be connected to or include a video display 832. The touch screen 824 may display graphic information relating to the IMD 10. The display 822 displays information related to the processes described herein. The touch screen 824 accepts a user's touch input 834 when selections are made. The keyboard 826 (e.g., a typewriter keyboard 836) allows the user to enter data to the displayed fields, as well as interface with the telemetry subsystem 830. Furthermore, custom keys 828 turn on/off 838 (e.g., EVVI) the external device 800. The printer 812 prints copies of reports 840 for a physician to review or to be placed in a patient file, and speaker 810 provides an audible warning (e.g., sounds and tones 842) to the user. The parallel I/O circuit 818 interfaces with a parallel port 844. The serial I/O circuit 820 interfaces with a serial port 846. The floppy drive 816 accepts diskettes 848. Optionally, the floppy drive 816 may include a USB port or other interface capable of communicating with a USB device such as a memory stick. The CD-ROM drive 814 accepts CD ROMs 850.

The telemetry subsystem 830 includes a central processing unit (CPU) 852 in electrical communication with a telemetry circuit 854, which communicates with both an intracardiac electrogram ("IEGM") circuit 856 and an analog out circuit 858. The circuit 856 may be connected to leads 860. The circuit 856 may also be connected to, or in communication with, implantable leads to receive and process cardiac signals as discussed above. Optionally, the cardiac signals sensed by the leads may be collected by the IMD 10 and then transmitted, to the external device 800, wirelessly to the telemetry subsystem 830 input.

The telemetry circuit 854 may be connected to a telemetry wand 862. The analog out circuit 858 includes communication circuits to communicate with analog outputs 864. The external device 800 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 800 to the IMD 10.

Figure 12:
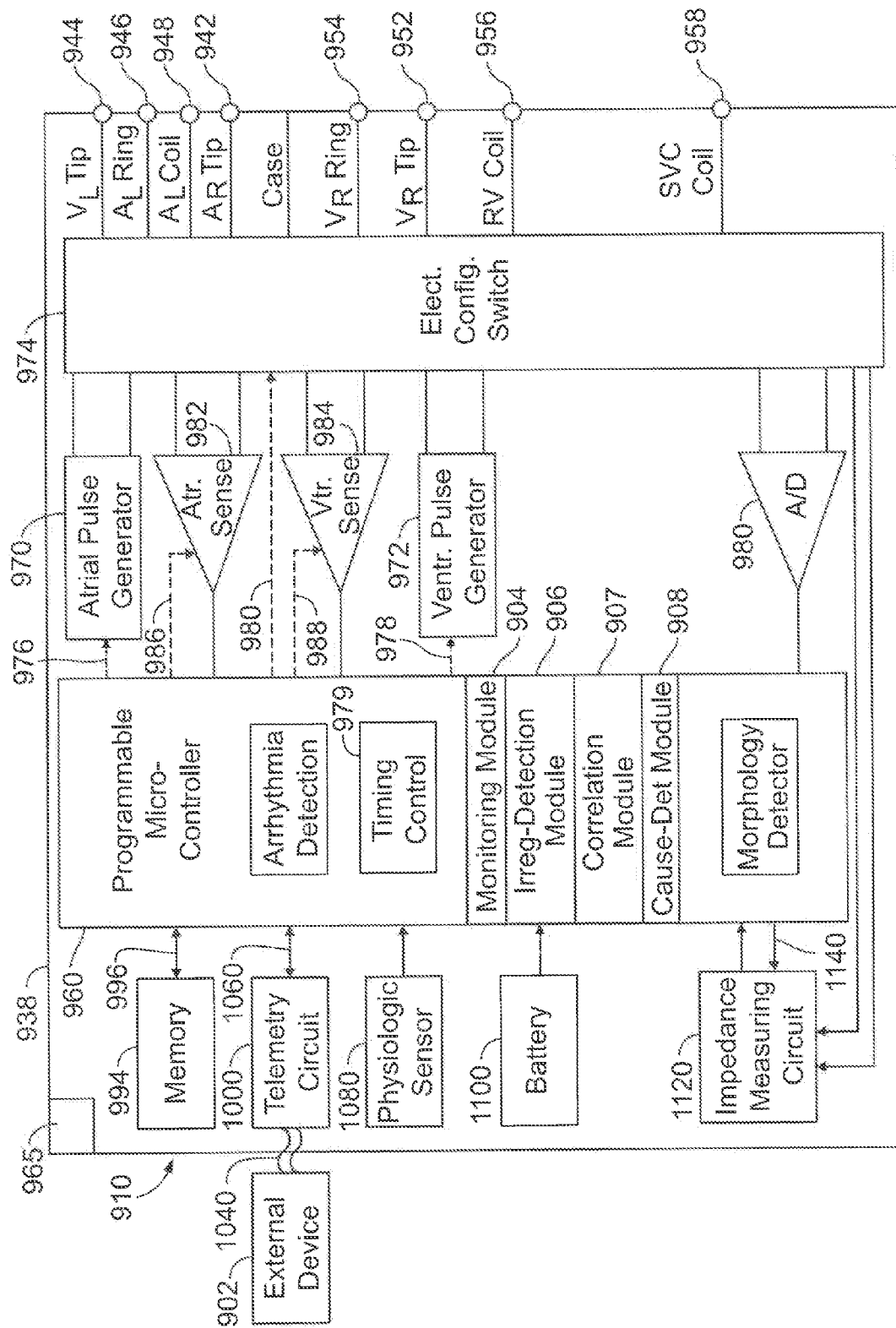
FIG. 12 illustrates a block diagram of exemplary internal components of an IMD 910, according to an embodiment.

FIG. 12 illustrates a block diagram of exemplary internal components of an IMD 910, according to an embodiment. The IMD 910 is for illustration purposes only, and it is understood that the circuitry could be duplicated, eliminated or disabled in any desired combination to provide a device capable of treating the appropriate chamber(s) with cardioversion, defibrillation and/or pacing stimulation as well as providing for apnea detection and therapy. The IMD 910 includes a housing 938, which is shown schematically in FIG. 12. The housing 938 is often referred to as the "can", "case" or "case electrode" and may be programmably selected to act as the return electrode for all "unipolar" modes. The housing 938 may further be used as a return electrode alone or in combination with one or more of the coil electrodes for shocking purposes. The housing 938 further includes a connector (not shown) having a plurality of terminals, 942, 952, 954, 956 and 958 (shown schematically and, for convenience, the names of the electrodes to which they are connected are shown next to the terminals). A right atrial tip terminal (A.sub.R TIP) 942 is adapted for connection to an atrial tip electrode and a right atrial ring terminal may be adapted for connection to a right atrial ring electrode. A left ventricular tip terminal (V.sub.L TIP) 944, a left atrial ring terminal (A.sub.L RING) 946, and a left atrial shocking terminal (A.sub.L COIL) 948 are adapted for connection to a left ventricular ring electrode, a left atrial tip electrode, and a left atrial coil electrode, respectively. A right ventricular tip terminal (V.sub.R TIP) 952, a right ventricular ring terminal (V.sub.R RING) 954, a right ventricular shocking terminal (R.sub.V COIL) 956, and an SVC shocking terminal (SVC COIL) 958 are adapted for connection to a right ventricular tip electrode, right ventricular ring electrode, an RV coil electrode, and an SVC coil electrode, respectively.

The IMD 010 includes a programmable microcontroller 960 which controls operation. The microcontroller 960 (also referred to herein as a processor module or unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 960 includes the ability to process or monitor input signals (data) as controlled by program code stored in memory. The details of the design and operation of the microcontroller 960 are not critical to the invention. Rather, any suitable microcontroller 960 may be used that carries out the functions described herein. Among other things, the microcontroller 960 receives, processes, and manages storage of digitized cardiac data sets from the various sensors and electrodes. For example, the cardiac data sets may include IEGM data, pressure data, heart sound data, and the like.

The IMD 910 includes an atrial pulse generator 970 and a ventricular/impedance pulse generator 972 to generate pacing stimulation pulses for delivery by the right atrial lead, the right ventricular lead, and/or the coronary sinus lead via an electrode configuration switch 974. It is understood that in order to provide stimulation therapy in each of the four chambers of the heart, the atrial and ventricular pulse generators, 970 and 972, may include dedicated, independent pulse generators, multiplexed pulse generators or shared pulse generators. The pulse generators, 970 and 972, are controlled by the microcontroller 960 via appropriate control signals, 976 and 978, respectively, to trigger or inhibit the stimulation pulses.

The microcontroller 960 further includes timing control circuitry 979 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 974 includes a plurality of switches for connecting the desired electrodes to the appropriate I/O circuits, thereby providing complete electrode programmability. Accordingly, the switch 974, in response to a control signal 980 from the microcontroller 960, determines the polarity of the stimulation pulses (e.g., unipolar, bipolar, etc.) by selectively closing the appropriate combination of switches (not shown) as is known in the art.

Atrial sensing circuit 982 and ventricular sensing circuit 984 may also be selectively coupled to the right atrial lead, coronary sinus lead, and the right ventricular lead, through the switch 974 for detecting the presence of cardiac activity in each of the four chambers of the heart. Accordingly, the atrial (ATR SENSE) and ventricular (VTR SENSE) sensing circuits, 982 and 984, may include dedicated sense amplifiers, multiplexed amplifiers or shared amplifiers. The outputs of the atrial and ventricular sensing circuits, 982 and 984, are connected to the microcontroller 960 which, in turn, are able to trigger or inhibit the atrial and ventricular pulse generators, 970 and 972, respectively, in a demand fashion in response to the absence or presence of cardiac activity in the appropriate chambers of the heart.

Cardiac signals are also applied to the inputs of an analog-to-digital (A/D) data acquisition system 990. The data acquisition system 990 is configured to acquire IEGM signals, convert the raw analog data into a digital IEGM signal, and store the digital IEGM signals in memory 994 for later processing and/or telemetric transmission to an external device 902. The data acquisition system 990 is coupled to the right atrial lead, the coronary sinus lead, and the right ventricular lead through the switch 974 to sample cardiac signals across any combination of desired electrodes.

As described above, the microcontroller 960 may include a monitoring module 904 configured to receive the position and physiologic data from inputs and monitor a physiologic characteristic of a patient. The microcontroller 960 may also include an irregularity-detection module 906 configured to detect an irregularity in the physiologic data, and a correlation module 907 configured to correlate the physiologic data with the position data. The microcontroller 960 may also include a cause-determination module 908 configured to determine a cause of the irregularity.

The irregularity-detection module 906 may be programmed to detect an irregularity by detecting an aberration in the position data. The aberration may be a deviation from a known baseline, template, waveform, or the like. For example, the aberration may be a deviation from a regular, repeating baseline, or a straight baseline.

The cause-determination module 908 may be programmed to determine that electromagnetic interference is the cause of an irregularity when the position data that correlates with the irregularity is steady (or otherwise does not deviate from a known baseline, template, waveform, or the like). The cause-determination module 908 may be programmed to determine that patient movement is the cause of an irregularity when the position data that correlates with the irregularity is associated with known position data readings related to patient movement. Additionally, the cause-determination module 908 may be programmed to determine that a lead fracture is the cause of the irregularity when the position data that correlates with the irregularity is associated with a known patient reading related to one or both of a patient movement or posture.

The microcontroller 960 is coupled to memory 994 by a suitable data/address bus 996, wherein the programmable operating parameters used by the microcontroller 960 are stored and modified, as required, in order to customize the operation of IMD 910 to suit the needs of a particular patient. The memory 994 also stores data sets (raw data, summary data, histograms, etc.), such as the IEGM data, heart sound data, pressure data, Sv02 data and the like for a desired period of time (e.g., 1 hour, 24 hours, 1 month, etc.). The memory 994 may store instructions to direct the microcontroller 960 to analyze the cardiac signals and heart sounds, identify characteristics of interest, and derive values for predetermined statistical parameters. The IEGM, pressure, and heart sound data stored in memory 994 may be selectively stored at certain time intervals, such as 5 minutes to 1 hour periodically or surrounding a particular type of arrhythmia of other irregularity in the heart cycle. For example, the memory 994 may store data for multiple non-consecutive 10 minute intervals.

The pacing and other operating parameters of the IMD 910 may be non-invasively programmed into the memory 994 through a telemetry circuit 1000 in telemetric communication with the external device 902, such as a programmer, transtelephonic transceiver or a diagnostic system analyzer, or with a bedside monitor. The telemetry circuit 1000 is activated by the microcontroller 960 by a control signal 1060. The telemetry circuit 1000 allows intra-cardiac electrograms, pressure data, acoustic data, Sv02 data, status information, and the like, as described above relating to the operation of IMD 910 (as contained in the microcontroller 960 or memory 994) to be sent to the external device 902 through an established communication link 1040.

The IMD 910 includes a position sensor or detector 965 which operates as discussed herein to generate posture signals that are used to identify an actual posture state of the patient.

The IMD 910 may also include an accelerometer or other physiologic sensor 1080, commonly referred to as a "rate-responsive" sensor because it is typically used to adjust pacing stimulation rate according to the exercise state of the patient. Optionally, the physiological sensor 1080 may further be used to detect changes in cardiac output, changes in the physiological condition of the heart, or changes in activity (e.g., detecting sleep and wake states) and to detect arousal from sleep. While shown as being included within IMD 910, it is to be understood that the physiologic sensor 1080 may also be external to IMD 910, yet still be implanted within or carried by the patient. A common type of rate responsive sensor is an activity sensor incorporating an accelerometer or a piezoelectric crystal, which is mounted within the housing 938 of IMD 910. The physiologic sensor 1080 may be used in conjunction with, or in place of, the position detector 965, for example.

The IMD 910 also includes a battery 1100, which provides operating power to all of the circuits shown. The IMD 910 is shown as having impedance measuring circuit 1120 which is enabled by the microcontroller 960 via a control signal 1140. Herein, impedance is primarily detected for use in evaluating ventricular end diastolic volume (EDV) but is also used to track respiration cycles. Other uses for an impedance measuring circuit include, but are not limited to, lead impedance, surveillance during the acute and chronic phases for proper lead positioning or dislodgement, detecting operable electrodes and automatically switching to an operable pair if dislodgement occurs, measuring respiration or minute ventilation; measuring thoracic impedance for determining shock thresholds; detecting when the device has been implanted, measuring stroke volume, and detecting the opening of heart valves, etc. The impedance measuring circuit 1120 is advantageously coupled to the switch 974 so that impedance at any desired electrode may be obtained.

Referring to FIGS. 1-12, embodiments provide a system and method of determining an irregularity in physiologic data, such as an intracardiac electrogram, through the use of position data output from a position detector, such as an accelerometer. The position data and the physiologic data may be correlated so that the a physician may quickly and easily determine the cause of the irregularity.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for determining a cause of an irregularity in physiologic data collected by an implanted medical device (IMD), the method comprising:
monitoring and storing a collected physiologic characteristic of a patient through the physiologic data in memory of the IMD, the physiologic data collected by the IMD;
detecting an irregularity in the physiologic data, wherein the irregularity is due to a non-motion cause that is unrelated to the physiologic characteristic being monitored;
monitoring and storing position data of the patient in the memory of the IMD, the position data collected by a position detector in the IMD;
automatically correlating the physiologic data with the position data; and
determining that electromagnetic interference is the non-motion cause of the irregularity in the physiologic data when the position data does not include an aberration correlated in time with the irregularity in the physiologic data.

2. The method of claim 1, wherein the detecting operation includes automatically reviewing the physiologic data by a controller of the IMD for a deviation from a standard baseline, waveform, steady state, or pattern as the irregularity.

3. The method of claim 1, wherein the correlating operation comprises synchronizing the physiologic data with the position data over a common time frame.

4. The method of claim 1, further comprising storing in the memory of the IMD, a flagged event from the position data, the flagged event representative of a patient posture, wherein the correlating operation comprises comparing the irregularity in the physiologic data with the flagged event from the position data.

5. The method of claim 1, wherein the determining operation comprises:
detecting that the position data that correlates with the irregularity is steady; and
determining that electromagnetic interference is the non-motion cause of the irregularity based on the steady position data.

6. The method of claim 1, wherein the determining operation comprises:
detecting that the position data that correlates with the irregularity is associated with known position data readings related to patient movement; and
determining that patient movement is a motion related cause of the irregularity based on the known position data readings.

7. The method of claim 1, further comprising continually storing the physiologic data and the position data in a memory of the IMD.

8. The method of claim 1, further comprising continually storing the physiologic data and the position data in a buffer within a memory of the IMD.

9. The method of claim 1, further comprising in response to detection of the irregularity, triggering recordation of the physiologic data and the position data in the memory of the IMD.

10. The method of claim 1, wherein the correlating operation is triggered in response to the detecting of the irregularity.

11. An implantable medical device comprising:
a main housing configured to be implanted within a patient;
a position detector, in the main housing, configured to provide position data of the patient; and
a controller contained within the main housing, the controller being configured to control operation of the IMD in order to extract physiologic data from a patient, wherein the controller comprises:
inputs to collect position data and physiologic data;
a monitoring module configured to receive the position and physiologic data from the inputs and monitor a physiologic characteristic of the patient;

an irregularity-detection module configured to detect an irregularity in the physiologic data, wherein the irregularity is due to a non-motion cause that is unrelated to the physiologic characteristic being monitored;

a correlation module configured to correlate the physiologic data with the position data; and a cause-determination module configured to determine that electromagnetic interference is the non-motion cause of the irregularity when the position data does not include an aberration correlated in time with the irregularity in the physiologic data.

12. The medical device of claim 11, wherein the position detector comprises a 3-axis accelerometer.

13. The medical device of claim 11, wherein the irregularity-detection module is configured to detect the irregularity by detecting whether an aberration occurs in the position data.

14. The medical device of claim 11, wherein the cause-determination module is configured to determine that electromagnetic interference is the non-motion cause of the irregularity when the position data that correlates with the irregularity is steady without the aberration.

15. The medical device of claim 11, wherein the cause-determination module is configured to determine that patient movement is a motion related cause of the irregularity when the position data that correlates with the irregularity is associated with known position data readings related to patient movement.

16. The medical device of claim 11, further comprising a memory within the main housing configured to store the physiologic data and the position data.

17. The medical device of claim 16, wherein the controller is configured to continually store the physiologic data and the position data in the memory.

18. The medical device of claim 16, wherein the controller is configured to continually store the physiologic data and the position data in a buffer within a memory of the IMD.

19. The medical device of claim 16, wherein the controller is configured to store the physiologic data and the position data in the memory when the irregularity is detected.

\* \* \* \* \*